United States Patent [19]

Leuthold et al.

[11] Patent Number: 5,494,035
[45] Date of Patent: Feb. 27, 1996

[54] METHOD FOR DETECTING PRESENCE OF FERROMAGNETIC OBJECTS IN A MEDICAL PATIENT

[75] Inventors: Arthur C. Leuthold; Ronald T. Wakai, both of Madison, Wis.

[73] Assignee: Wisconsin Alumni Research Foundation, Madison, Wis.

[21] Appl. No.: 329,736

[22] Filed: Oct. 26, 1994

[51] Int. Cl.$^6$ ........................................................ A61B 5/05
[52] U.S. Cl. ................... 128/653.1; 324/248; 324/261; 128/782
[58] Field of Search ................... 128/653.1, 782; 324/244, 259–261, 248

[56] References Cited

U.S. PATENT DOCUMENTS

| | | | |
|---|---|---|---|
| 4,804,915 | 2/1989 | Hoenig | 324/259 |
| 4,922,916 | 5/1990 | Ermert et al. | 128/653.1 |
| 4,995,395 | 2/1991 | Ilmoniemi et al. | 128/653.1 |
| 5,018,724 | 5/1991 | Naser et al. | 128/653.1 |
| 5,265,609 | 11/1993 | Buchanan et al. | 128/653.1 |
| 5,384,109 | 1/1995 | Klaveness et al. | 128/653.1 |

OTHER PUBLICATIONS

Article entitled "MR Procedures and Biomedical Implants, Materials, and Devices: 1993 Update" from Nov. 1993 issue of Radiology, pp. 587–599.

*Primary Examiner*—Krista M. Zele
*Assistant Examiner*—Brian L. Casler
*Attorney, Agent, or Firm*—Quarles & Brady

[57] ABSTRACT

Medical patients are screened prior to magnetic resonance imaging by using a superconducting quantum interference device magnetometer to detect the unknown presence of an implanted ferromagnetic object. The patient is placed on a table which vibrates at approximately five Hertz. The magnetometer is sequentially held stationary at a plurality of positions adjacent to the patient being vibrated. The magnetic field intensity is measured at each position with the magnetometer and the magnetic field measurements are used to determine the presence and location of a ferromagnetic object within the patient.

12 Claims, 1 Drawing Sheet

METHOD FOR DETECTING PRESENCE OF FERROMAGNETIC OBJECTS IN A MEDICAL PATIENT

BACKGROUND OF THE INVENTION

The present invention relates to magnetic resonance imaging, and more particularly to methods for detecting the presence of a ferromagnetic object within a medical patient to be imaged.

Magnetic resonance imaging (MRI) is a common modality used in medical diagnosis. An MRI system utilizes very strong magnetic fields to cause precession of the magnetic moments of the nuclei of atoms within the medical patient. The magnetic moments are aligned by radio frequency magnetic fields and the decay of such alignment is detected. The nuclei of different atoms decay at various rates, thereby enabling use of the detected decay characteristics of different regions within the patient to create an image of internal organs.

Numerous surgical procedures permanently insert metallic objects, such as ocular implants, heart valve protheses, stents and orthopedic implants. Magnetic resonance imaging may be contraindicated for an individual with implanted ferromagnetic material, because of the risk associated with movement or dislodgement of the implanted object. In addition, other possible hazards exist, including the induction of electric currents in the ferromagnetic object, excessive heating and misinterpreting an image artifact caused by the object as an abnormality.

In the case of surgically implanted ferromagnetic materials, the patient usually knows of their existence and can communicate that fact to the physician or technician performing the magnetic resonance imaging. However, the presence of such surgical implants may not be known in situations where the patient is unconscious or otherwise cannot communicate with the medical personnel, as often occurs with accident victims. In addition, patients may not be aware of the presence of other ferromagnetic objects, such as a metal shard which accidentally became embedded in the patient's body. Therefore, a patient who is to undergo magnetic resonance imaging may not know or be able to inform the medical personnel about the presence of internal ferromagnetic objects.

Previous procedures for screening medical patients prior to MRI presumed that the patient was aware of both the presence and precise nature of the ferromagnetic object. Such information was used to look up the implanted object in a table that also listed the magnetic properties to different types of devices which could be present within a patient. A table of this type is given in an article entitled, "MR Procedures and Biomedical Implants, Materials, and Devices: 1993 Update," *Radiology*, November 1993, pages 587–599. However, such screening methods can not be used in situations where the patient is unaware of an object's presence or exact type.

Therefore, it is desirable to provide a method for not only detecting the presence of ferromagnetic material within a medical patient, but the ferromagnetic properties of the object.

Conventional metal detectors, such as those used to locate objects under the sand on a beach, cannot be utilized to detect relatively small ferromagnetic objects, such as a metal shard. Even such small objects can create serious problems during MRI due to the very intense magnetic fields employed. Furthermore, common metal detectors determine the presence of a metallic object by sensing high electrical conductivity. Because the primary hazards during MRI relate to the magnetic characteristics of implants, conductivity based detection does not accurately portray the hazard potential during imaging. It should be noted that the conductivity of an object does not indicate the magnetic characteristics.

SUMMARY OF THE INVENTION

A general objective of the present invention is to provide a method for determining the presence of unknown ferromagnetic material within a medical patient, such as a patient about to undergo magnetic resonance imaging.

Another objective is to provide a method for determining the magnitude of the ferromagnetic properties of such an object.

A further objective of the present invention is to provide a technique for locating ferromagnetic objects within a medical patient.

These and other objectives are achieved by a method which employs a magnetometer to detect the presence of an unknown ferromagnetic object implanted in a medical patient. The magnetometer, such as a superconducting quantum interference device, is held in a stationary position and adjacent to the medical patient. The medical patient is moved with respect to the magnetometer, for example by vibrating the patient at less than ten Hertz. The magnetometer measures the intensity of the magnetic field adjacent to the patient being moved and the measurement is used to determine whether a ferromagnetic object is present within the patient.

DESCRIPTION OF THE PREFERRED EMBODIMENT

Figure 1:
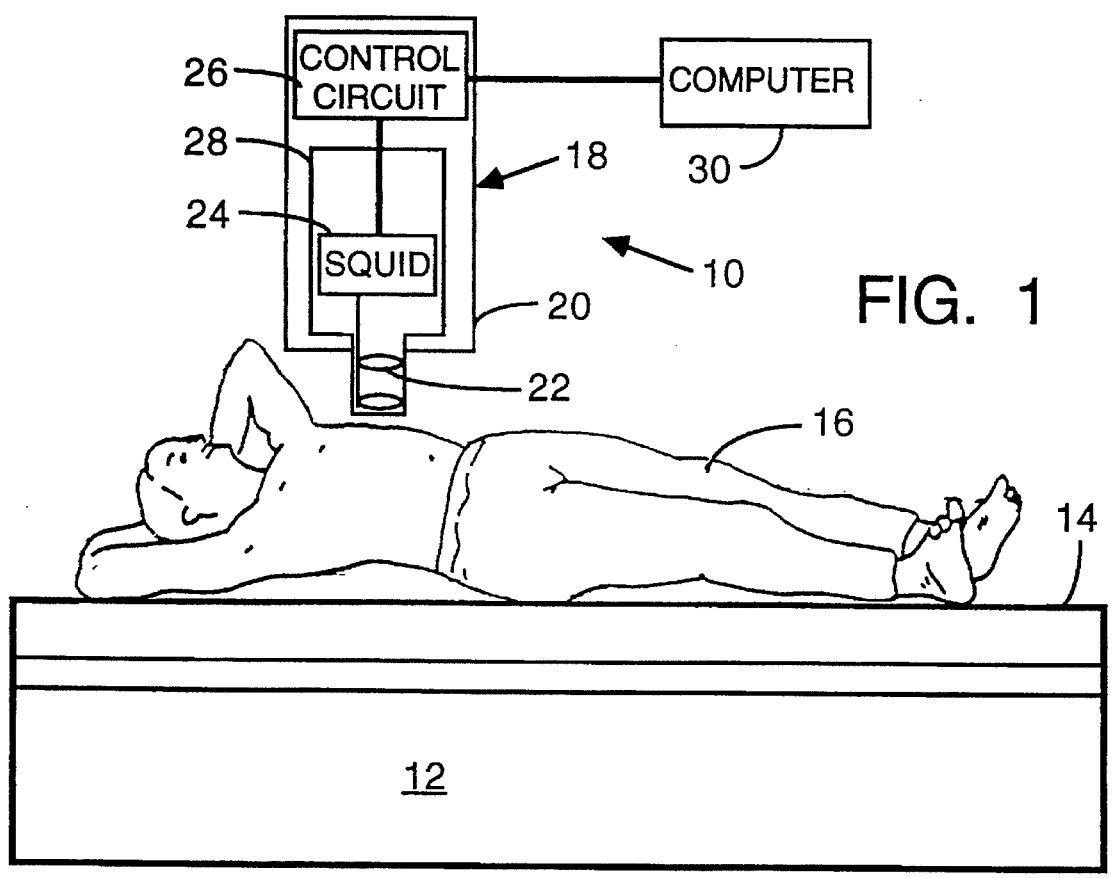
FIG. 1 is a schematic diagram of an apparatus employed to practice the present invention.

With reference to the drawing, a ferromagnetic object detection apparatus 10 includes a table 12 with an upper surface 14 on which the medical patient 16 lies. The table 12 includes a mechanism for vibrating the upper surface 14 either in the horizontal or vertical direction. A magnetometer 18 is placed adjacent the patient. Although different types of magnetometers may be used, either a fluxgate or a superconducting quantum interference device (SQUID) are preferred. Magnetometer 18 shown in the drawing is a SQUID type device which is particularly preferred because of its high sensitivity.

The standard magnetometer 18 includes a dewar 20 that contains a set of electrical coils 22 connected to a SQUID 24, which components become superconductive when immersed in liquid nitrogen or liquid helium in reservoir 28. SQUID 24 is interfaced to a remote computer 30 by a conventional control circuit 26. The computer 30 converts the output signal from the SQUID into a measurement of the flux intensity of the magnetic field and displays the result via an operator interface. SQUID magnetometers of this type have been employed to measure magnetic flux produced by electric currents within the human body due to brain or heart activity.

All ferromagnetic objects produce a magnetic field, even though the object has not been intentionally magnetized. The magnetic fields from objects implanted in humans are relatively weak and vary depending upon the size of the object and its constituent metal. An extremely sensitive apparatus is required to detect such small magnetic fields in order to sense the presence of an implant and determine the implant's ferromagnetic characteristics.

During the present patient screening process, the dewar 20 the magnetometer is moved in steps over the patient 16. At each step the dewar 20 is held stationary while the region of the patient's body beneath the coils 22 is being examined. The stepping continues until all regions of interest have been examined.

If the magnetometer is moved during the sensing, ambient magnetic field gradients within the examining room will be detected by the magnetometer 18 and adversely affect object detection. As a consequence, the present method holds the dewar 20 stationary while examining a region of the patient's body. To vary the magnetic field from a ferromagnetic object within the patient's body, the surface of the table 12 is vibrated in either the horizontal or the vertical direction at ten Hertz or less, with five Hertz being preferred for example. The magnetometer measures the time varying magnetic flux at the surface of the patient's body and displays the measurement to the physician or MRI technician via the operator interface of computer 30. Relatively high magnetic field intensity indicates the presence of a ferromagnetic object within the region of the medical patient being examined.

Once the presence of a ferromagnetic object is located, further inquiry of the patient or an X-ray is taken to determine the nature of the object and its precise location within the patient.

An alternate method can be used which may improve detection of weekly magnetized particles. In doing so, a uniform magnetic field is generated around the patient, such as by placing the patient in a Helmholtz coil. The strength of the uniform magnetic field is considerably less than an MRI magnetic field and thus ferromagnetic objects will not be moved by the field. However, a ferromagnetic object within the patient's body will distort the uniform magnetic field. As the patient is vibrated on the table, the field distortion is detected by the magnetometer.

We claim:

1. A method for detecting presence of an unknown ferromagnetic object in an animal, which method comprises:
   (a) placing a magnetometer in a stationary position and adjacent to the animal;
   (b) moving the animal with respect to the magnetometer;
   (c) measuring a magnetic field with the magnetometer while the animal is being moved, to produce thereby a magnetic field measurement; and
   (d) determining, from the magnetic field measurement produced by the magnetometer, whether a ferromagnetic object is present within the animal.

2. The method recited in claim 1 wherein the magnetometer includes a superconducting quantum interference device.

3. The method as recited in claim 1 wherein the magnetometer is a fluxgate magnetometer.

4. The method as recited in claim 1 wherein the moving step comprises vibrating the animal.

5. The method as recited in claim 1 wherein the moving step comprises vibrating the animal at a frequency that does not exceed ten Hertz.

6. The method as recited in claim 1 further comprising placing the animal in a uniform magnetic field; detecting a distortion of the uniform magnetic field with the magnetometer, wherein the distortion is due to the presence of the animal in the uniform magnetic field; and determining, from the detected distortion of the uniform magnetic field, a size of the ferromagnetic object within the animal.

7. The method as recited in claim 1 further comprising placing the magnetometer at a plurality of positions adjacent the animal and holding the magnetometer stationary at each position while performing steps (b) through (d).

8. A method for screening a medical patient prior to magnetic resonance imaging to detect the presence of an unknown ferromagnetic object, which method comprises steps of:

vibrating the the medical patient;

sequentially holding a magnetometer stationary at a plurality of positions adjacent to the medical patient;

at each one of the plurality of positions, measuring a magnetic field with the magnetometer while the medical patient is being vibrated, to produce thereby a plurality of magnetic field measurements; and determining, from the plurality of magnetic field measurements produced by the magnetometer, whether a ferromagnetic object is present within the medical patient.

9. The method as recited in claim 8 further comprises determining, from the magnetic field measurements and positions of the magnetometer at which the magnetic field measurements were made, a location of a ferromagnetic object within the medical patient.

10. The method as recited in claim 8 wherein the vibrating step comprises vibrating the medical patient at a frequency that does not exceed ten Hertz.

11. The method recited in claim 8 wherein the magnetometer includes a superconducting quantum interference device.

12. The method as recited in claim 8 wherein the magnetometer is a fluxgate magnetometer.

* * * * *